United States Patent [19]

Hartung

[11] Patent Number: 4,811,732
[45] Date of Patent: Mar. 14, 1989

[54] PROTECTIVE BREATHING APPARATUS HAVING BREATHING AIR CIRCULATION

[75] Inventor: Karl-Heinz Hartung, Northumberland, Great Britain

[73] Assignee: Draegerwerk AG, Fed. Rep. of Germany

[21] Appl. No.: 90,427

[22] Filed: Aug. 26, 1987

Related U.S. Application Data

[63] Continuation of Ser. No. 779,525, Sep. 24, 1985, abandoned.

[30] Foreign Application Priority Data

Apr. 25, 1985 [DE] Fed. Rep. of Germany ....... 3515030

[51] Int. Cl.⁴ ............................................. A61M 16/00
[52] U.S. Cl. ........................... 128/204.26; 128/204.28; 128/205.11; 128/205.17
[58] Field of Search ....................... 128/204.26, 204.27, 128/203.28, 205.11–205.18, 204.28

[56] References Cited

U.S. PATENT DOCUMENTS

| | | | |
|---|---|---|---|
| 958,427 | 5/1910 | Panian | 128/205.13 |
| 2,711,170 | 6/1955 | Bornstein | 128/205.13 |
| 2,737,176 | 3/1956 | Fox | 128/205.17 |
| 2,907,322 | 10/1959 | Hay | 128/204.28 |
| 2,924,215 | 2/1960 | Goodner | 128/205.13 |
| 3,316,965 | 5/1967 | Seeler | 128/204.28 |
| 3,358,681 | 12/1967 | Chabanier | 128/205.13 |
| 3,402,711 | 9/1968 | Emerson | 128/204.28 |
| 3,473,531 | 10/1968 | Tatham | 128/205.17 |
| 3,616,053 | 1/1972 | Medwick | 128/205.17 |
| 3,827,432 | 8/1974 | Lundgren et al. | 128/205.17 |
| 4,195,627 | 4/1980 | Haertle | 128/205.17 |
| 4,299,216 | 11/1981 | Bernard et al. | 128/205.17 |

FOREIGN PATENT DOCUMENTS

| | | | |
|---|---|---|---|
| 919628 | 9/1954 | Fed. Rep. of Germany . | |
| 716976 | 10/1966 | Italy | 128/205.12 |

Primary Examiner—Edward M. Coven
Assistant Examiner—K. M. Reichle
Attorney, Agent, or Firm—McGlew & Tuttle

[57] ABSTRACT

A protective breathing apparatus with breathing air circulation and addition of oxygen alone through a lung-controlled valve is to be improved so that no oxygen depletion of the breathing air in the circulation occurs, even if the breath volumes are small, and that preflushing the circulation with oxygen before applying the protective breathing apparatus is unnecessary. In addition to a breathing bag space, a storage space, unfoldable during the exhaling phase and unchangeable during the inhaling phase, is provided in the circulation.

3 Claims, 2 Drawing Sheets

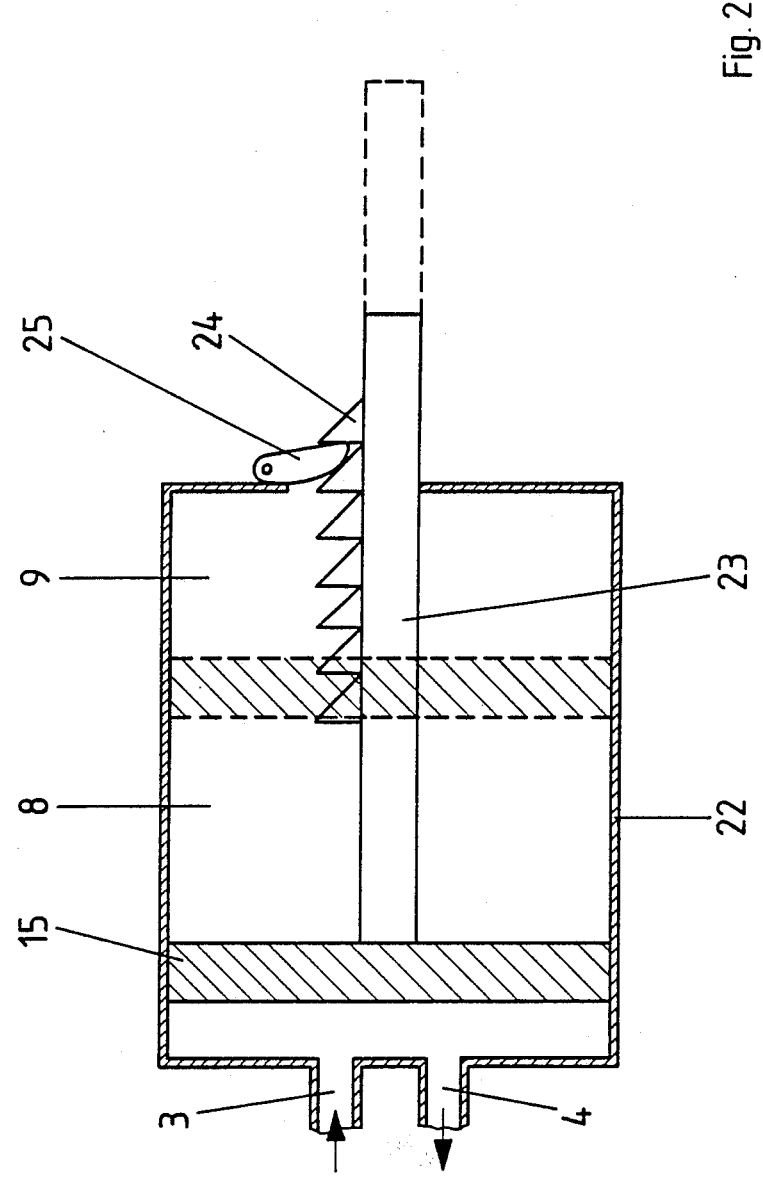

PROTECTIVE BREATHING APPARATUS HAVING BREATHING AIR CIRCULATION

This application is a continuation of application Ser. No. 779,525, filed Sept. 24, 1985, now abandoned.

FIELD AND BACKGROUND OF THE INVENTION

The invention relates in general to respirators and in particular to a new and useful protective breathing apparatus with breathing air circulation and with addition of oxygen alone through a lung controlled valve.

A similar protective breathing apparatus is described in German patent application No. 919,628. In the known protective breathing apparatus, the breathing bag, the lines carrying breathing gas, and the regeneration unit are flushed with pure oxygen before applying the mouthpiece so that the wearer of the apparatus can inhale from a full breathing bag flushed with oxygen and return his exhaled air into it again. If a larger amount of breathing air is inhaled, the collapsing breathing bag actuates a lever mechanism which opens a valve to add oxygen to the inhale line. The breathing bag is kept to a minimum volume by the inflowing oxygen. When the wearer of the known protective breathing apparatus puts it on and exhales his first full breath into the protective breathing apparatus, then, assuming the worst case, the nitrogen component from his lungs mixes with the oxygen in the protective breathing apparatus. While a part of this mixture leaves the breathing circulation through a pressure relief valve, because breathing bag was already filled by the oxygen flushing the system, oxygen from the supply in the breathing bag is constantly consumed by the apparatus wearer during the subsequent inhale phases, and a constant oxygen depletion occurs in the protective breathing apparatus circulation during the subsequent breathing cycles. Especially at low volume inhale phases it may take several breathing cycles to empty the breathing bag to the point where the lung controlled valve responds and feeds pure oxygen into the breathing bag. In the meantime, however, the oxygen depletion can have progressed so far that the last inhaled breaths no longer contain enough oxygen for the apparatus wearer. This oxygen depletion, which is equivalent to a nitrogen enrichment, can bring the apparatus wearer into undesirable situations.

Beyond this, the dosing parts and supply lines needed to flush the breathing circulation with oxygen are costly, require additional space in the apparatus housing and increase the weight of the protective breathing apparatus.

SUMMARY OF THE INVENTION

The invention provides an improved protective breathing apparatus wherein, even in an escape apparatus, no oxygen depletion of the breathing air in the circulation occurs even if the inhaled breath volumes are small. No preflushing of the circulation with oxygen is necessary before the protective breathing apparatus is used.

In accordance with the invention, a storage space unfoldable during the exhale phase and unchangeable during the inhale phase is provided in the circulation in addition to a breathing bag.

The advantage of the invention is to be seen in that the apparatus wearer, immediately after putting the protective breathing apparatus on by applying the mouthpiece, rids his exhaled volume of $CO_2$ with the exhaled first breath. The wearer exhales into the storage space, unfolding the storage space in a first step without thereby filling the breathing bag itself. Since during the next inhalation phase the lung controlled valve responds immediately because of the still empty breathing bag, making pure oxygen available to the apparatus wearer for inhaling, he exhales during the next exhalation phase an oxygen enriched exhaled volume into the storage space, thus filling it further. The breathing cycle repeats in this manner until the storage space is full. It now contains breathing air with an oxygen content higher than the concentration in the ambient air. Only after the storage space is filled after several breathing cycles does this oxygen enriched breathing gas overflow into the breathing bag. The oxygen enriched breathing gas in the breathing bag is now available to the apparatus wearer so that the breathing bag is emptied by a subsequent inhaled breath. If the breathing bag content suffices for one breath, the lung controlled valve will not respond. But if a greater gas volume is needed for inhaling than the breathing bag contains, this excess requirement is made available from the oxygen tank through the now responding lung controlled valve, but not from th breathing gas in the storage space. If the wearer starts his or her use of the apparatus on an inhalation phase then all initial breathing gas is supplied over the lung controlled valve and as pure oxygen.

Accordingly, the breathing circulation, after the application of the protective breathing apparatus is first filled by the apparatus wearer with exhaled air enriched with oxygen before he can inhale from the breathing bag.

Some of the nitrogen component originally present in the apparatus wearer's lungs gets into the storage space. Since the storage space cannot be emptied again by inhaling, the entire original nitrogen component cannot get directly back to the lungs again either. Therefore, there always remains room in the lungs to absorb additional oxygen. Due to the initial unfolding of the storage space through air exhaled by the apparatus wearer with corresponding intake of oxygen through the lung controlled valve, the oxygen component of breathing air in the circulation is increased.

Also when subsequent breathing is shallow so that the breathing bag is not completely emptied, the breathing bag is filled up again by oxygen enriched breathing air with the subsequently exhaled volume of air.

Since the exhaled air goes into the additional storage space, the dwelling time of the purified exhaled air to the next inhalation is prolonged considerably so that an effective cooling takes place.

It has proved to be of advantage to dimension the storage space volume by the breathing bag volume. Typically, they are 3.5:1, although the volume of the storage space may also be larger.

Even though the storage space may basically be disposed anywhere in the breathing circulation, a particularly favorable configuration is seen in combining the storage space and the breathing bag into one unit. Thus, one common housing may be provided for both the storage space and the breathing bag in simple manner so that the storage space, once unfolded, can be expanded by the volume of the breathing bag.

In another embodiment of the invention the storage space may be formed by having a limiting device engage the variable breathing bag so that the former cannot contract below a specifiable residual volume. Such a limiting device may be, for instance, a sliding locking mechanism or a valve actuated by the expansion of the unit.

Another purposeful embodiment of the invention is achieved in that the storage space and the breathing bag are divided by a partitioning wall containing a transfer element through which the oxygen enriched breathing air can flow from the storage space into the breathing bag as long as a specified storage space gas content limit is exceeded.

If the storage space has movable walls, the transfer element may expediently be opened by a suitable actuator after reaching a specified storage space volume so that, in a subsequent exhalation into the storage space, oxygen enriched breathing air can overflow from the space into the breathing bag.

A valve of known design may be provided as the transfer element. Slide valves may alternately be connected to the movable wall parts such as by pulling chains.

Another advantageous embodiment of the transfer element is designed as a valve responding to the differential pressure between the storage space and the breathing bag. The differential pressure governing the opening of the valve is determined in that it is composed of the storage space pressure limit increased by the response pressure of the lung controlled valve. This ensures that when inhaling from the insufficiently filled breathing bag, the lung controlled valve is opened due to the underpressure prevailing in the inhalation branch, and not the valve in the partitioning wall. This prevents breathing air from being sucked out of the storage space into the breathing bag through the development of an underpressure in the inhalation branch.

Such a valve is advantageously also suited for use as an additional safety valve to the transfer element in the partitioning wall.

Accordingly it is an object of the invention to provide a protective breathing apparatus in which the breathing air is circulated through exhale and inhale lines through a storage space which includes an unfoldable part operable during the exhaling phase and which is unchangeable during the inhaling phase and with a lung control valve connection from an oxygen tank which supplies oxygen into the air circulation.

A further object of the invention is to provide a protective breathing apparatus which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 2 is a schematic view of another embodiment of the storage space and breathing bag.

DESCRIPTION OF THE PREFERRED EMBODIMENTS

Figure 1:
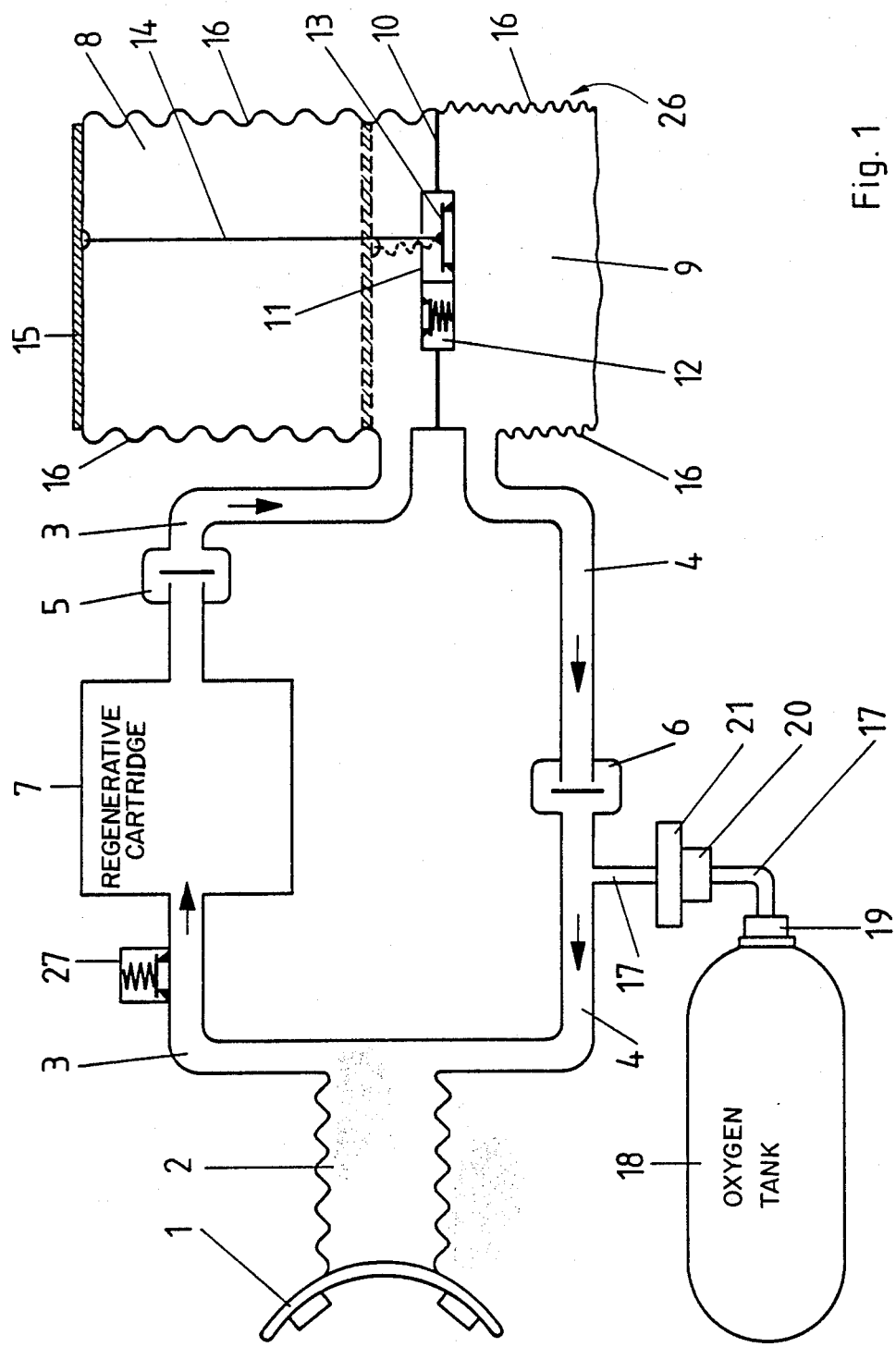
FIG. 1 is a schematic plan view of a protective breathing apparatus with a first embodiment of the storage space and breathing bag.

Referring to the drawings in particular, the invention embodied therein comprises a protective breathing apparatus which includes a patient or user connection line 2 having a mouth engaging portion 1 for a patient or user. An exhale line 3 and an inhale line 4 are connected to the connection line 2. Oxygen is added to the inhale line 4 through a lung controlled oxygen supply including a supply line 17 connected to an oxygen tank 18.

In accordance with the invention, a storage space unit generally designated 26 is connected to the exhale line 3 and the inhale line 4. The storage space unit 26 includes a first storage space portion 8 and a breathing bag space portion 9. The first storage space portion 8 has an expanding part defined by bellows walls 16, and it is connected to the exhale line 3. The unit 26 also has valve means in a transfer element 11 associated therewith permitting it to expand during exhalation. The user is assumed to inhale and exhale with an inhaled and an exhaled volume of gas.

The protective breathing apparatus shown in FIG. 1 comprises a mouthpiece 1 connected by a connecting hose 2 to both the exhale line 3 and the inhale line 4. Disposed in both the exhale line 3 and the inhale line 4 is a check valve 5 and 6 each of which assure the breath flow direction during a breathing cycle, as indicated by the arrows. The exhale line 3 contains a regeneration cartridge 7 which binds the $CO_2$ in the exhaled gas. In front of the regeneration cartridge 7 is a pressure relief valve 27. The exhale line 3 ends inside a storage space 8, and the inhale line 4 starts at a breathing bag 9. The storage space 8 and the breathing bag 9 are combined to form a storage space unit 26 and the spaces are separated from each other by a partitioning wall 10. Disposed in the partitioning wall 10 are a transfer element 11 including a dish-type valve 13 and a spring loaded safety valve 12. The dish valve 13 of the transfer element 11 is connected to a movable wall part 15 defining storage spaced by a connecting cord 14. The other wall parts of both the storage space 8 and breathing bag 9 are bellows walls 16. An oxygen tank 18 containing a tank valve 19 is connected to the inhale line 4 via a connecting line 17. Disposed in the connecting line 17 are a pressure reducer 20 and a lung controlled valve 21.

To operate the protective breathing apparatus, the apparatus wearer applies the mouthpiece 1 and takes, for example, a deep initial inhalation breath from the inhale line 4. At least initially the volume of the breathing bag 9 is insufficient for inhalation so that the lung controlled valve 21 is actuated by the underpressure in the inhale line 4, and oxygen from the tank 18 flows through the connecting line 17 into the inhale line 4. The inhaled air, thus oxygen enriched, enters the apparatus wearer's lungs through the connecting hose 2 and the mouthpiece 1. In the lungs, the oxygen is consumed and the $CO_2$ given off to the exhaled air. This exhaled air is filled into the initially empty volume of the storage space 8 through the exhale line 3, the $CO_2$ binding regeneration cartridge 7 and the check valve 5. Since the movable wall part 15 of the storage space 8 is in its initial position shown in dotted lines, it is raised by an amount corresponding to the volume of the exhaled air. The apparatus wearer's subsequent inhalation generates an underpressure in the inhale line 4 because the breathing bag 9 was emptied by the preceding inhalation or initially empty so that the lung controlled valve 21 responds immediately and the apparatus wearer inhales pure oxygen through the mouthpiece 1. The apparatus wearer's lungs absorb a small amount of oxygen and the rest of the inhaled oxygen mixes with the nitrogen still contained in the lungs. The air, now exhaled, is highly oxygen enriched and is freed of $CO_2$ in the regeneration cartridge via the exhale line 3 and conducted into the storage space 8. The movable wall part 15 now moves by another amount. This described cycle repeats until the movable wall part 15 has moved to its fully extended end position shown in FIG. 1. More oxygen enriched exhaled air supplied through the exhale line 3 lifts the dish membrane of valve 13 due to the pull on a connecting cord 14. Accordingly, with each subsequent exhalation a volume corresponding to the exhaled volume flowing into the storage space 8 is transferred from the storage space 8 into the breathing bag 9. The breathing gas requirement going beyond the inhalation volume contained in the breathing bag 9 is furnished through the lung controlled valve 21 from the oxygen tank 18. If the apparatus wearer's breathing gas requirement is less than the volume contained in the breathing bag 9, the breathing bag is emptied partly by breathing; while in the subsequent exhalation, however, a volume reduced by the oxygen consumption is transferred from the oxygen enriched storage space 8 into the breathing bag 9. The circulating volume, therefore, is automatically adapted to the prevailing breathing conditions.

The cord 14 acts as accumulation means operatively interconnected with the storage space 8 and bag 9 to permit space 8 to expand only up to its maximum volume.

FIG. 2 shows another embodiment of storage space and breathing bag. It comprises e.g. a cylindrical housing 22 in which a piston 15 is guided by the piston rod as movable wall part. Fastened to a piston rod 23 secured to the piston 15 is a rack 24, between the teeth of which a pawl 25 engages. The inhale line 3 and the exhale line 4 are only shown as attachments. They continue as complete lines as in FIG. 1.

In this other embodiment, the piston 15 is shown in its basic position at the time the breathing apparatus is applied. The apparatus wearer's first inhalation from the inhale line 4 will leave the piston 15 in its basic position because of the engaged pawl 25. The apparatus wearer inhales pure oxygen through the lung controlled valve 21 and through the exhale line 3, gives off $O_2$ enriched exhaled air to the interior of the housing 22 defined by the piston 15.

The piston 15 moves in accordance with the exhaled volume, and the rack 24 is pushed past the pawl 25 by a corresponding amount. The pawl engages again, retaining the piston 15 during the next inhalation from the inhale line 4 so that the apparatus wearer must automatically inhale pure oxygen. This process repeats until the piston 15 has been pushed so far out of the housing 22 that the rack 24 is completely past the pawl 25. The interior section thus formed represents the unchangeable storage space 8. Further exhalations can push the piston 15 up to the face of housing 22 which contains the pawl 25. The additional, variable space thus formed is to be considered the breathing bag 9.

While specific embodiments of the invention have been shown and described in detail to illustrate the application of the principles of the invention, it will be understood that the invention may be embodied otherwise departing from such principles.

What is claimed is:

1. A protective breathing apparatus for a user inhaling a volume of gas and exhaling a volume of gas, comprising: a user connection line adapted for connection to the user; an inhale line connected to said connection line; a first check valve in said inhale line for permitting passage of gas only toward said connection line through said inhale line; an exhale line connected to said connection; a second check valve in said exhale line for permitting passage of gas only from said connection line through said exhale line; lung controlled oxygen supply means connected to said inhale line for supplying oxygen to said inhale line upon a falling of pressure in said inhale line due to the unsatisfied demand of the user; a storage space unit connected to said inhale line and to said exhale line, said storage space unit including a partition wall dividing said storage space unit into a first storage space portion, which includes the connection to said exhale line and a breathing bag space portion, which includes the connection to said inhale line; said first storage space portion comprising a wall opposite from said partition wall and a first expandable bellows connected between said wall and said partition wall, the volume defined by said first storage space portion being expandable up to a maximum volume comprising at least a plurality of exhalation volumes of the user, said breathing bag space portion comprising a breathing bag sealingly connected to the surface of said partition wall opposite said first storage space portion and a transfer means connected through said partition wall for opening communication between said first storage space portion and said breathing bag space portion only after said maximum volume of said first storage space portion has been reached.

2. A protective breathing apparatus according to claim 1 wherein said transfer means comprises a transfer valve in said partition wall having a valve seat, closing means and a connecting cord connected between said closing means and said opposite wall dimensioned to move said closing means to an open position when said maximum volume of said first storage space is reached.

3. A protective breathing apparatus according to claim 2 including a safety valve in said partition wall having a valve seat, a closing means and means for biasing said closing means against said valve seat closing communication between said first storage space portion and said breathing bag space portion until a selected presssure in said first storage space portion is reached, which is higher than that in said breathing bag space portion.

* * * * *